(12) United States Patent
Yaszemski et al.

(10) Patent No.: US 7,163,545 B2
(45) Date of Patent: Jan. 16, 2007

(54) SPINAL CORD SURGICAL IMPLANT

(75) Inventors: Michael J. Yaszemski, Rochester, MN (US); Jonathan A. Friedman, Rochester, MN (US); Michael J. Moore, Rochester, MN (US); Anthony J. Windebank, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 260 days.

(21) Appl. No.: 10/629,427

(22) Filed: Jul. 29, 2003

(65) Prior Publication Data

US 2004/0102793 A1 May 27, 2004

Related U.S. Application Data

(60) Provisional application No. 60/399,250, filed on Jul. 29, 2002.

(51) Int. Cl.
*A61B 17/08* (2006.01)
(52) U.S. Cl. ............... 606/152; 606/153; 606/154; 606/155; 424/423; 424/426
(58) Field of Classification Search ............... 606/76, 606/77, 152, 153, 154, 155; 424/423, 424, 424/426
See application file for complete search history.

(56) References Cited

U.S. PATENT DOCUMENTS

| 4,273,920 A | | 6/1981 | Nevin |
| 4,870,966 A | * | 10/1989 | Dellon et al. ............... 606/152 |
| 5,061,281 A | * | 10/1991 | Mares et al. ............... 424/426 |
| 5,358,475 A | * | 10/1994 | Mares et al. ............... 523/113 |
| 5,656,605 A | | 8/1997 | Hansson et al. |
| 5,681,568 A | * | 10/1997 | Goldin et al. ............ 424/184.1 |
| 5,736,132 A | * | 4/1998 | Juergensen et al. ........ 424/94.5 |
| 5,874,099 A | | 2/1999 | Dionne et al. |
| 5,925,053 A | | 7/1999 | Hadlock et al. |
| 6,063,378 A | | 5/2000 | Nohara et al. |
| 6,132,360 A | | 10/2000 | Halpern |
| 6,214,021 B1 | | 4/2001 | Hadlock et al. |

(Continued)

OTHER PUBLICATIONS

Olmarker et al., "Chondroitinase ABC (Pharmaceutical Grade) for Chemonucleolysis", Spine, 1996. 21:1952-56.

(Continued)

*Primary Examiner*—Michael J. Hayes
*Assistant Examiner*—Michael G. Mendoza
(74) *Attorney, Agent, or Firm*—Quarles & Brady LLP (57) ABSTRACT

An implant for bridging a gap in a severed spinal cord or nerve and for promoting nerve regeneration has a matrix comprising a biocompatible, biodegradable, polymeric material. The matrix has a proximal end for connection to a first end of severed spinal cord and a distal end for connection to a second end of severed spinal cord. The matrix includes internal guidance channels extending between the proximal end and the distal end to facilitate rejoining of the first end and the second end of the severed spinal cord. A bioactive agent may be dispersed in the matrix, or disposed in the channels, or included within microspheres in the channels. The channels may be arranged such that guidance channels correspond to spinal cord tracts. Alternatively, guidance channels may be spaced apart at the proximal end of the matrix and converge inward toward the axis of the matrix at the distal end.

27 Claims, 4 Drawing Sheets

1. POST. SPINOCEREBELLAR TR.
2. FASC. CUNEATUS
3. FASC. GRACILIS
4. LAT. CORTICOSPINAL TR.
5. SPINOTHALAMIC TR.
6. RUBROSPINAL TR.
7. PONTINE RETICULOSPINAL TR.
8. ANT. CORTICOSPINAL TR.
9. VESTIBULOSPINAL TR.
10. MEDULLARY RETICULOSPINAL TR.

U.S. PATENT DOCUMENTS

| | | | |
|---|---|---|---|
| 6,241,771 | B1 | 6/2001 | Gresser et al. |
| 6,362,308 | B1 | 3/2002 | Pham |
| 6,368,630 | B1 | 4/2002 | Bernstein et al. |
| 6,471,993 | B1* | 10/2002 | Shastri et al. ............... 424/486 |
| 6,716,225 | B1* | 4/2004 | Li et al. ..................... 606/152 |
| 6,972,168 | B1* | 12/2005 | Muir ........................... 435/1.1 |
| 2002/0051806 | A1* | 5/2002 | Mallapragada et al. ..... 424/423 |
| 2002/0086047 | A1* | 7/2002 | Mueller et al. ............. 424/426 |

OTHER PUBLICATIONS

Bradbury et al., "Chondroitinase ABC promotes functional recovery after spinal cord injury", Nature, Apr. 11, 2002, 416:636-40.

Zuo et al., "Regeneration of Axons after Nerve Transection Repair is Enhanced by Degradation of Chondroitin Sulfate Proteoglycan", Exp. Neurol., 2002. 176:221-28.

Oldham et al., "Biological Activity of rhBMP-2 Released from PLGA Microspheres", Journal of Biomechanical Engineering, 2000. 122:289-292.

Farndale, "Improved quantitation and discrimination of sulphated glycosaminoglycans by use of dimethylmethylene blue", Biochemica et Biopphysica Acta, 1986. 883:173-77.

* cited by examiner

1. POST. SPINOCEREBELLAR TR.
2. FASC. CUNEATUS
3. FASC. GRACILIS
4. LAT. CORTICOSPINAL TR.
5. SPINOTHALAMIC TR.
6. RUBROSPINAL TR.
7. PONTINE RETICULOSPINAL TR.
8. ANT. CORTICOSPINAL TR.
9. VESTIBULOSPINAL TR.
10. MEDULLARY RETICULOSPINAL TR.

SPINAL CORD SURGICAL IMPLANT

CROSS-REFERENCES TO RELATED APPLICATIONS

This application claims the benefit of U.S. Provisional Patent Application No. 60/399,250 filed Jul. 29, 2002.

STATEMENT REGARDING FEDERALLY SPONSORED RESEARCH

Not Applicable.

BACKGROUND OF THE INVENTION

1. Field of the Invention

This invention relates to a biodegradable polymer device for surgical implantation in patients with spinal cord injury.

2. Description of the Related Art

Despite significant advances in our understanding of neurophysiology and spinal cord injury, a patient who sustains a complete spinal cord injury has only a small hope of recovery. Loss of neurologic function following complete spinal cord injury remains a devastating condition. Research has not yet yielded an effective way to stimulate the neuronal axons to regrow to replace the injured axonal structures. Current interventions offer little hope for recovery of neurologic function in patients following complete spinal cord injury, in either the acute or chronic setting.

Devices for promoting nerve regeneration have been proposed. See, for example, U.S. Pat. Nos. 6,214,021 and 5,925,053. Progress has been made in elucidating mechanisms that facilitate or inhibit axon regeneration in the spinal cord. Despite these advances, functional recovery following spinal cord injury in experimental models has been insufficient to bring reconstructive therapy to clinical trial. Combinations of several therapeutic strategies may be important.

Thus, there remains a need for devices and methods that promote axon regeneration in the spinal cord. In particular, there is a need for an implant for bridging a gap in a severed spinal cord or nerve and for promoting nerve regeneration.

SUMMARY OF THE INVENTION

The foregoing needs are met by a biodegradable polymer device according to the invention for surgical implantation in patients with spinal cord injury. The device comprises an implant for bridging a gap in a severed spinal cord or nerve and for promoting nerve regeneration. The implant comprises a matrix comprising a biocompatible, biodegradable, polymeric material. The matrix has a proximal end for connection to a first end of a severed spinal cord or nerve and a distal end for connection to a second end of the severed spinal cord or nerve. The matrix includes a plurality of internal guidance channels extending between the proximal end of the matrix and the distal end of the matrix to facilitate rejoining of the first end of the severed spinal cord or nerve and the second end of the severed spinal cord or nerve. A bioactive agent may be dispersed in the matrix, or disposed in the channels, or included within microparticles disposed in the channels. The channels may be arranged such that the guidance channels correspond to spinal cord tracts when the implant is positioned in a gap in a severed spinal cord. Alternatively, the guidance channels may be spaced apart adjacent a perimeter of the matrix at the proximal end of the matrix and converge inward toward the axis of the matrix at the distal end of the matrix.

It is therefore an advantage of the present invention to provide a biodegradable polymer implant which functions both as a scaffold to support axon growth and as a site for the controlled local delivery of bioactive agents which promote axon regeneration.

It is another advantage of the present invention to provide a biodegradable polymer implant which provides for the controlled local delivery of bioactive agents which promote axon regeneration from the implant matrix.

It is yet another advantage of the present invention to provide a biodegradable polymer implant which provides for the controlled local delivery of bioactive agents which promote axon regeneration from channels within the implant matrix.

It is still another advantage of the present invention to provide a biodegradable polymer implant which provides for the controlled local delivery of bioactive agents which promote axon regeneration from microspheres disposed in channels within the implant matrix.

It is yet another advantage of the present invention to provide a biodegradable polymer implant which functions as a scaffold that supports axon growth through internal guidance channels in the implant matrix that correspond to spinal cord tracts.

It is still another advantage of the present invention to provide a biodegradable polymer implant which functions as a scaffold that supports axon growth through internal guidance channels in the implant matrix that are spaced apart at the proximal end of the matrix and converge inward toward the axis of the matrix at the distal end thereby funneling regenerating axons from proximal white matter tracts to more permissive gray matter distal to the implant.

These and other features, aspects, and advantages of the present invention will become better understood upon consideration of the following detailed description, drawings, and appended claims.

BRIEF DESCRIPTION OF THE DRAWINGS

Like reference numerals will be used to refer to like or similar parts from Figure to Figure in the following description.

DETAILED DESCRIPTION OF THE INVENTION

The present invention is directed to a biocompatible, biodegradable polymer device for surgical implantation in patients with spinal cord injury. The biodegradable polymer implant functions both as a scaffold to support axon growth and a site for the controlled local delivery of agents which promote axon regeneration. As a scaffold, the microarchitecture of the implant can be engineered for optimal axon growth and organization. As a site for the delivery of pro-regenerative agents, the implant provides local delivery and controlled release over time.

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. As used herein, a "bioresorbable" material is one that breaks down over a finite period of time due to the chemical/biological action of the body.

In one version of the invention, the implant for bridging a gap in a severed spinal cord or nerve and for promoting nerve regeneration comprises a matrix including a biocompatible, biodegradable, polymeric material and a bioactive agent dispersed within the matrix. The matrix has a proximal end for connection to a first end of a severed spinal cord or nerve and a distal end for connection to a second end of the severed spinal cord or nerve. The matrix includes a plurality of internal guidance channels extending between the proximal end of the matrix and the distal end of the matrix to facilitate rejoining of the first end of the severed spinal cord or nerve and the second end of the severed spinal cord or nerve.

The bioactive agent is selected depending on the physiological effect desired. A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, ribozymes, organometallics, proteins, glycoproteins, peptides, polyamino acids, antibodies, nucleic acids, steroidal molecules, antibiotics, antimycotics, cytokines, carbohydrates, oleophobics, lipids, extracellular matrix and/or its individual components, mammalian cells, genetically engineered cells, pharmaceuticals, and therapeutics. In nerve regeneration applications, advantageous bioactive agents include, without limitation, proteoglycan degrading enzymes, preferably chondroitinase, and most preferably chondroitinase ABC.

The bioactive agent is "dispersed" within the matrix if the bioactive agent is directly or indirectly, physically or chemically bound to the matrix at a location other than, or in addition to, the surface of the matrix. A bioactive agent may be physically bound to the matrix by dispersing, entrapping, imbedding or otherwise containing a bioactive agent within the matrix. For example, coprecipitation techniques may be used to achieve physical association. A bioactive agent may be chemically bound to the matrix by way of a chemical reaction wherein the bioactive agent is covalently or ionically bonded to the matrix. Thus, various techniques for dispersing the bioactive agent in the matrix of the implant are contemplated. Dispersing the bioactive agent in the matrix of the implant can provide for advantageous controlled release of the bioactive agent when the implant is positioned within the body. For example, the matrix may release the bioactive agent in a sustained manner (and most preferably linear manner) after an initial burst release.

In another version of the invention, the implant for bridging a gap in a severed spinal cord or nerve and for promoting nerve regeneration comprises a matrix including a biocompatible, biodegradable, polymeric material. The matrix has a proximal end for connection to a first end of a severed spinal cord or nerve and a distal end for connection to a second end of the severed spinal cord or nerve. The matrix includes a plurality of internal guidance channels extending between the proximal end of the matrix and the distal end of the matrix to facilitate rejoining of the first end of the severed spinal cord or nerve and the second end of the severed spinal cord or nerve. A bioactive agent is disposed in at least some of the channels of the implant. In this version of the invention, the bioactive agent may be as described above. In nerve regeneration applications, Schwann cells (i.e., any of the cells that cover the nerve fibers in the peripheral nervous system and form the myelin sheath) are advantageous bioactive agents. However, it has been discovered that bioactive agents other than Schwann cells are also advantageous, whether used alone or in combination with other bioactive agents (which may include Schwann cells).

Figure 1A:
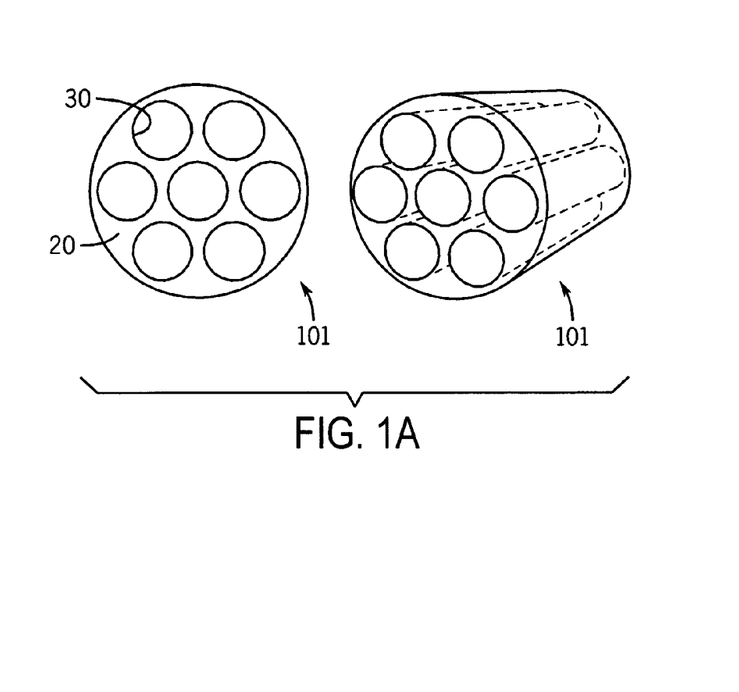
FIG. 1A shows a cross-sectional view and a longitudinal perspective view of a polymer implant according to the invention.
Figure 1B:
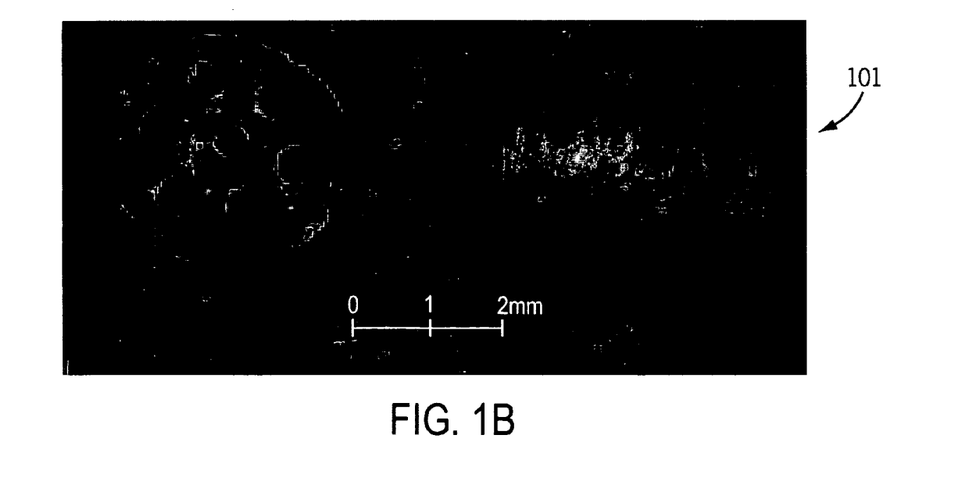
FIG. 1B shows a cross-sectional view and side view of a poly(lactide-co-glycolide) (PLGA) (85:15 lactide/glycolide) implant prepared according to the invention.

An example implant according to the invention is shown in FIGS. 1A and 1B, and can be constructed of a poly (lactide-co-glycolide) biocompatible, biodegradable material, (PLGA) (e.g., 85:15 ratio lactide/glycolide), with a uniform array of parallel, cylindrical guidance channels 30 within the matrix 20 of the implant 101. While poly(lactide-co-glycolide) is a preferred polymeric material for forming the matrix 20 of the implant 101, other biocompatible, biodegradable polymers may be used such as polycaprolactone and copolymers of lactic acid and glycolic acid. A Teflon® polytetrafluoroethylene mold and wire apparatus can be used to produce these implants. One embodiment of the implants for use in the rat spinal cord is cylindrical, 3 millimeters in diameter and 3 millimeters in length, and each guidance channel has a diameter of 450 µm. Other implants for use in the rat spinal cord are cylindrical, 3 millimeters in diameter and 2 millimeters in length, and each guidance channel has a diameter of 450 µm and/or 600 µm. Synthesis techniques have proven to be consistent and reproducible. One embodiment of the implant 101 uses a uniform array of channels 30 as described and depicted in FIGS. 1A and 1B. The guidance channels for axon growth may be filled with a bioactive agent as described above including, without limitation, a Schwann cell suspension and/or Chondroitinase ABC. The guidance channels for axon growth may also be filled with microparticles including a bioactive agent as described above. FIG. 1B shows cross-sectional and side views of a PLGA (85:15 lactide/glycolide) implant 101 prepared according to the invention.

Still referring to FIGS. 1A and 1B, the guidance channels 30 within the implant 101 may be loaded with a Schwann cell suspension to act as a scaffold for axon growth. Schwann cells have been cultured from newborn rat sciatic nerve, harvested and suspended in Matrigel brand matrix at a density of $120 \times 10^6$ cells/ml. The Schwann cell suspension was injected by micropipette into each channel of the implant, filling the channel as confirmed by gross inspection and microscopy. Implants were loaded with Schwann cells in this manner and incubated in tissue culture medium at 37° C. for 48 hours. Paraffin embedding and histologic examination revealed viable Schwann cells throughout the channels of the implant.

In pilot animal studies, implants without Schwann cells were implanted into transected rat spinal cords at T9 to assess local tissue response. Spinal cord with implant was harvested at 3, 7, or 11 days following implantation. The implant had remained well-positioned in all cases, and there was no gross evidence of inflammation. At 7 and 11 days following implantation, the tissue incorporation of the implant into the spinal cord was sufficient to remove the proximal and distal spinal cord with the graft as one piece, and suspend in fixative. Histologic examination revealed tissue ingrowth at the interfaces between implant and spinal cord. Cellular tissue elements had invaded the full length of the implant at 7 and 11 days post-implantation. There was no evidence of inflammatory response at the cellular level.

In yet another version of the invention, the implant provide a device for bridging a gap in a severed spinal cord and for promoting nerve regeneration. The implant has a matrix comprising a biocompatible, biodegradable, polymeric material. The matrix has a proximal end for connection to a first end of a severed spinal cord and a distal end for connection to a second end of the severed spinal cord. The matrix includes a plurality of internal guidance channels extending between the proximal end of the matrix and the distal end of the matrix to facilitate rejoining of the first end of the severed spinal cord and the second end of the severed spinal cord. The guidance channels are arranged such that the guidance channels correspond to spinal cord tracts when the implant is positioned in the gap in the severed spinal cord.

Figure 2:
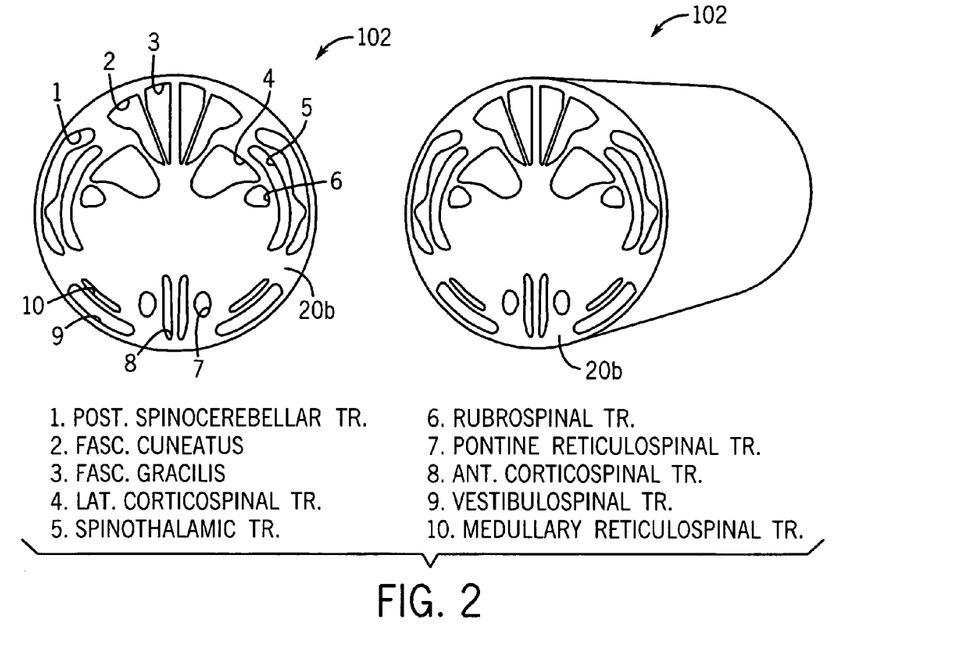
FIG. 2 shows a cross-sectional view and a longitudinal perspective view of a second embodiment of an implant according to the invention with guidance channels corresponding to key spinal cord tracts.

This embodiment of the implant 102 is shown in FIG. 2, and uses an architecture in which guidance channels correspond to spinal cord tracts, to enhance functional organization of regenerating axons. FIG. 2 shows cross-sectional and perspective longitudinal views of an implant 102 with guidance channels corresponding to key spinal cord tracts. This design can enhance functional organization of regenerating axons. In FIG. 2, there are shown in the matrix 20b separate guidance channels for: 1. Post. spinocerebellar tr.; 2. Fasc. Cuneatus; 3. Fasc. Gracilis; 4. Lat. Corticospinal tr.; 5. Spinothalamic tr.; 6. Rubrospinal tr.; 7. Pontine reticulospinal tr.; 8. Ant. Corticospinal tr.; 9. Vestibulospinal tr.; and 10. Medullary reticulospinal tr.

In still another version of the invention, the implant for bridging a gap in a severed spinal cord or nerve and for promoting nerve regeneration comprises a matrix including a biocompatible, biodegradable, polymeric material. The matrix has a proximal end for connection to a first end of a severed spinal cord or nerve and a distal end for connection to a second end of the severed spinal cord or nerve. The matrix includes a plurality of internal guidance channels extending between the proximal end of the matrix and the distal end of the matrix to facilitate rejoining of the first end of the severed spinal cord or nerve and the second end of the severed spinal cord or nerve. The guidance channels are spaced apart adjacent a perimeter of the matrix at the proximal end of the matrix and converge inward toward the axis of the matrix at the distal end of the matrix.

Figure 3A:
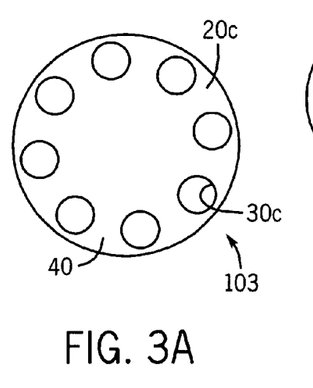
FIG. 3A shows a cross-sectional view at the proximal interface of a third embodiment of an implant according to the invention having guidance channels designed to funnel regenerating axons from proximal white matter tracts to more permissive gray matter distal to the implant.
Figure 3B:
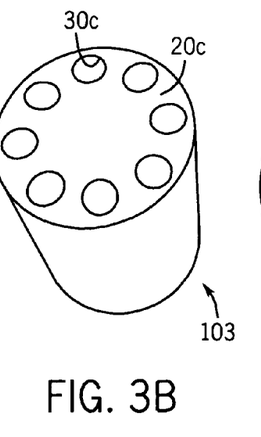
FIG. 3B shows a transparent longitudinal perspective view of the implant of FIG. 3A.
Figure 3C:
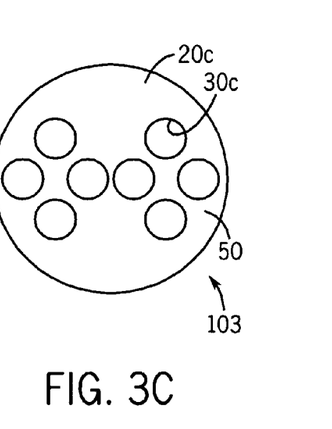
FIG. 3C shows a cross-sectional view of a distal interface of the implant of FIG. 3A.

This embodiment of the implant 103 shown in FIGS. 3A, 3B and 3C has guidance channels 30c that funnel axons from white matter to the potentially more permissive gray matter. In other words, the guidance channels 30c at the first end 40 of the implant 103 are arranged near the periphery of the implant 103 and the guidance channels 30c move inward toward the axis of the implant 103 such that the guidance channels 103 are nearer the axis at the second end 50 of the implant 103.

The polymer matrix 20, 20b, 20c between the channels 30, 30b, 30c can serve as structural support and a reservoir for sustained release of one or more bioactive agents. Chondroitin sulfate proteoglycans have been identified as key inhibitory factors in the complex local cellular response to spinal cord injury. Administration of chondroitinase ABC (C-ABC), an enzyme which degrades a variety of chondroitin sulfate proteoglycans, significantly enhanced axon regeneration in vitro and following brain, spinal cord, and peripheral nerve lesions in rats. Because of its substantial therapeutic potential, experiments were conducted in incorporating C-ABC into the biodegradable polymer implant. Different methods can be used to incorporate C-ABC or any other bioactive agent into the implant. First, the bioactive agent (e.g., C-ABC) can be directly introduced (i.e., dispersed) in the polymer as described above. Second, the bioactive agent (e.g., C-ABC and/or Schwann cells) can be layered on the surface of the implant and/or within guidance channels. The bioactive agent may be suspended in a suitable carrier such as Matrigel brand matrix for surface layering or placement in the guidance channels. Third, microspheres (e.g., PLGA with an average diameter=50 μm) can be created for encapsulation and sustained-release delivery of the bioactive agent (e.g., C-ABC). The microspheres can be layered on the surface of the implant and/or within guidance channels. Optionally, the microspheres including the bioactive agent may be suspended in a suitable carrier such as Matrigel brand matrix for surface layering or placement in the guidance channels.

EXAMPLES

The following Examples have been presented in order to further illustrate the invention and are not intended to limit the invention in any way.

Example 1

Multichannel Scaffolds for Axon Regeneration in the Spinal Cord

1A. Introduction

Biodegradable materials were investigated for their use as conduits for peripheral nerve repair, and these strategies were adapted for use in the injured spinal cord. However, the spinal cord has a highly organized fascicular arrangement, so single-channel guidance conduits may not represent the optimum geometry for guiding axonal regeneration after complete spinal cord injury. Example 1 describes fabrication techniques for constructing biodegradable scaffolds with multiple-channel, complex architectures. These scaffolds were studied for their ability to provide sustained drug delivery in vitro, and axon regeneration in vivo.

1B. Methods

Scaffolds with parallel-channel architecture were fabricated by injecting a 50% (w/v) solution of poly-(lactic-co-glycolic acid) (PLGA), with a copolymer ratio of 85:15 lactide to glycolide, in dichloromethane (DCM) into a 3-mm diameter Teflon mold fitted with a uniform array of stainless-steel wires with diameters of 508 or 660 millimeters each. Molds were placed in a vacuum chamber to remove the DCM before separation. Fluorescein isothiocyanate (FITC)-dextran (Mw 145 kD) served as a model drug and was incorporated into scaffolds before injection into molds. Scaffolds were placed in PBS (pH 7.4) at 37° C., and this fluid was monitored periodically for FITC-dextran release by spectrophotometric absorption at 490 nm. Scaffold degradation was monitored by mass loss and molecular weight loss. The molecular weight was measured by gel permeation chromatography.

Schwann cells were harvested from neonatal Sprague-Dawley (SD) rat sciatic nerves, suspended in Matrigel brand matrix at a density of $1.2 \times 10^8$ cells/ml., and injected into the channels of the polymer scaffolds. Adult female SD rats were anesthetized, and their spinal cords were completely transected at level T8–10. Cell-seeded scaffolds were inserted directly into the spinal canal before closure. Spinal cord tissue was harvested at 30, 60 and 90 days postoperatively, fixed in paraformaldehyde, and stained with an anti-neurofilament antibody. Scaffolds were imaged with X-ray micro-CT, and tissue sections viewed with light microscopy. Additionally, a Solidscape PatternMaster 3-D printer was used in conjunction with computer-aided design (CAD) software to construct molds with complex architecture for injection of PLGA.

1C. Results and Discussion

Figure 4:
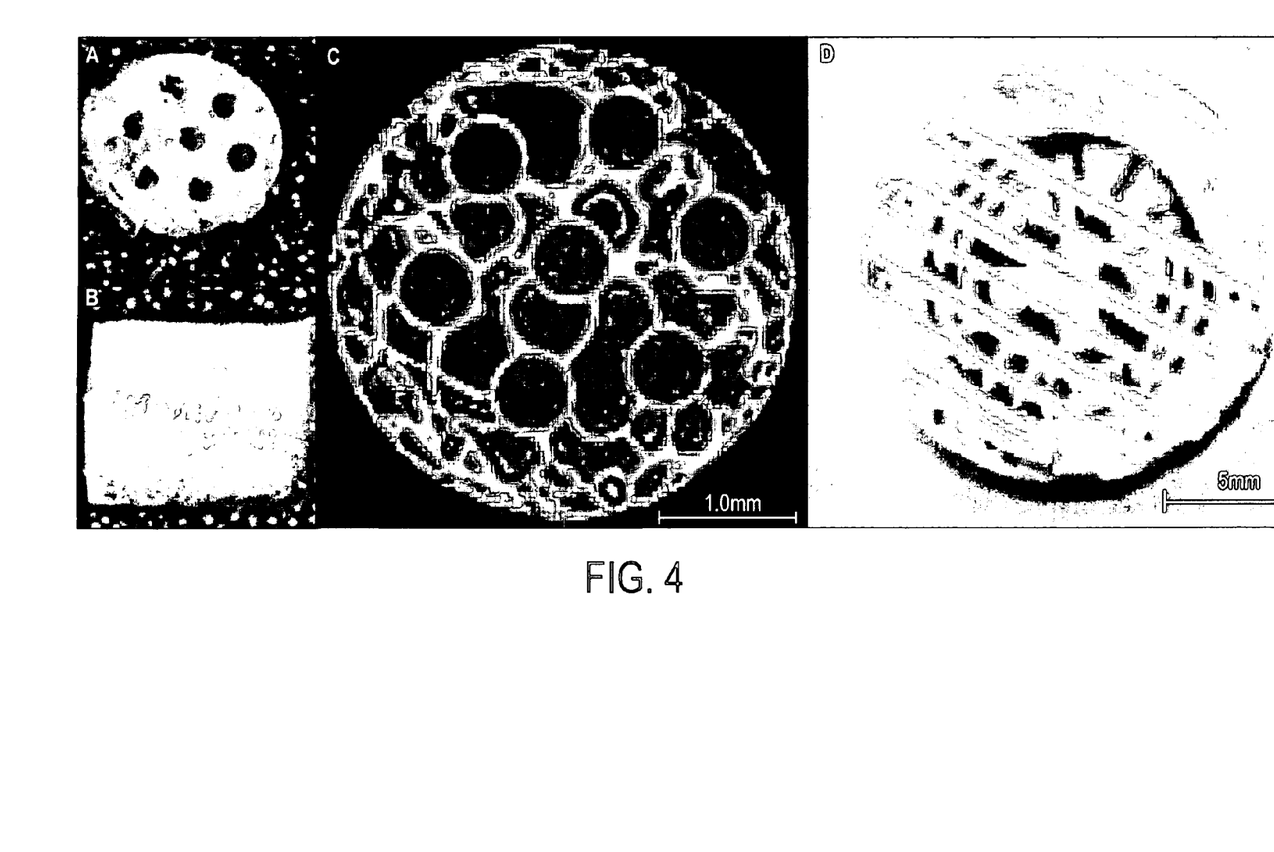
FIG. 4 shows: A) a cross-sectional photograph and B) a side view photograph of a biodegradable scaffold with parallel channel architecture; C) an internal micro-CT slice (2-D) of a scaffold revealing highly porous structure; and D) a 3-D printed, wax mold for creation of scaffolds with complex architecture consistent with spinal cord anatomy.
Figure 5:
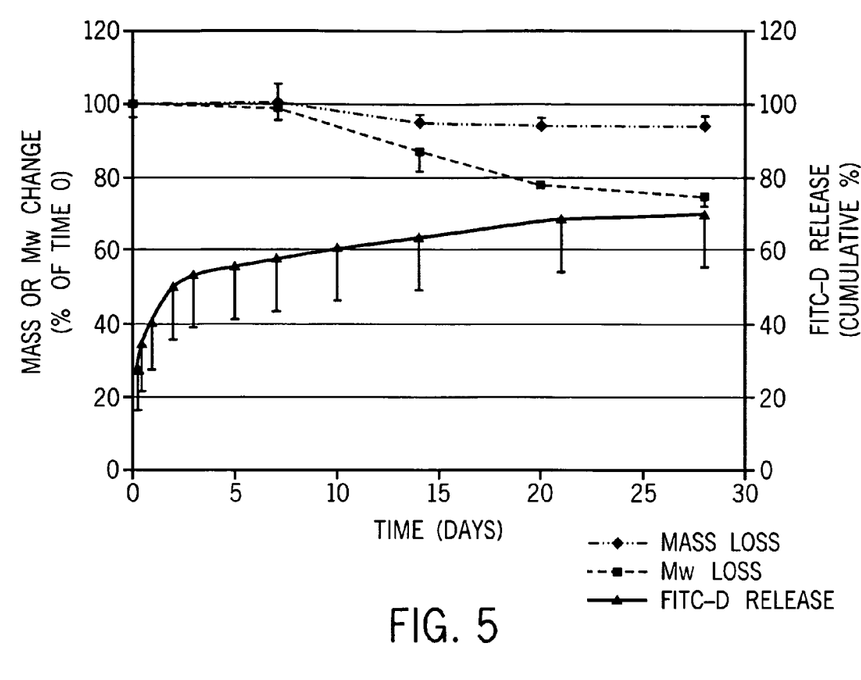
FIG. 5 shows the degradation of scaffolds and sustained release of FITC-dextran in vitro. Degradation is measured as mean mass or molecular weight change, in % of time 0; error bars indicate ± standard deviation, n=3. Drug release is cumulative % of total incorporated drug; bars indicate standard error of the mean for 2 experimental groups, each with n=5.

Fabrication yielded polymer scaffolds with large, open, parallel channels, surrounded by a porous sponge-like matrix (see FIG. 4). Implants incubated at 37° C. for 48 hours in tissue culture medium contained viable Schwann cells suspended in the channels. At one, two, and three months post-implantation, histology revealed extensive neurofilament staining, indicating axons entering and traveling through the length of the implant, as well as the presence of accompanying capillaries. FITC-dextran release occurred with an initial burst of about 50% of the incorporated dose, followed by sustained release over a period of at least one month (see FIG. 5). 3-D printed molds with specific architecture could be filled with PLGA, supporting the feasibility of solid freeform fabrication to mimic spinal cord architecture (see FIG. 4). These fabrication techniques allow for creation of drug-delivering scaffolds with longitudinal channels in specific arrangements that facilitate axon guidance.

Example 2

Release of Chondroitinase ABC from PLGA Microparticles

2A. Introduction

Chondroitinase ABC (C-ABC) has been investigated for clinical chemonucleolysis of herniated intervertebral discs (see Olmarker et al., *Spine*, 1996. 21:1952–56), and recently it has been used experimentally for in vitro and in vivo degradation of proteoglycans involved in glial scarring in central (see Bradbury et al., *Nature*, 2002. 416:636–40) and peripheral nervous system injury (see Zuo et al., *Experimental Neurology*, 2002.176:221–28). Sustained, local delivery of C-ABC may therefore prove useful for multiple clinical applications. Experiments with release of C-ABC from polymer microparticles were conducted. The activity of C-ABC after release from PLGA (85-15) microparticles was investigated. Activity was examined as a decrease in absorbance, which is calculated by subtracting experimental values from blank microparticle values. The control was calculated by subtracting an aqueous positive control from the aqueous negative control. FITC-dextran (molecular weight 100,000) was also used as a marker to mimic release from identical microspheres of a compound with molecular weight similar to C-ABC.

2B. Methods

C-ABC was purchased from Seikagaku Corp. (Tokyo) and encapsulated with bovine serum albumin (BSA) in poly-(lactic-co-glycolic acid) (PLGA) using a double emulsion, solvent extraction technique described previously by Oldham et al. in the *Journal of Biomechanical Engineering*, 2000. 122:289–292. Microparticle (MP) preparations were made containing 1 unit (1×), 10 units (10×), and 50 units (50×) C-ABC per 250 mg. PLGA.

Microparticles in quantities of 25 mg were sealed in nylon pouches and placed in a sodium acetate buffer containing 30 mg/ml chondroitin sulfate A (ChS-A). At multiple time points, pouches were removed and placed in fresh buffer solution. Blank microparticles served as a negative control, and fresh aqueous C-ABC added at each time point served as a positive control.

Aliquots were removed and mixed with a dimethyl-methylene blue (DMMB) dye, which changes color in the presence of sulfated glycosaminoglycans (see Farndale et al., *Biochemica et Biophysica Acta*, 1986. 883:173–77). The color change was monitored by measuring absorbance at 525 nm. on a spectrophotometer. Increased absorbance corresponds to an increased concentration of ChS-A, so enzymatic activity of C-ABC corresponds with a decrease in absorbance.

2C. Results and Discussion

Figure 6:
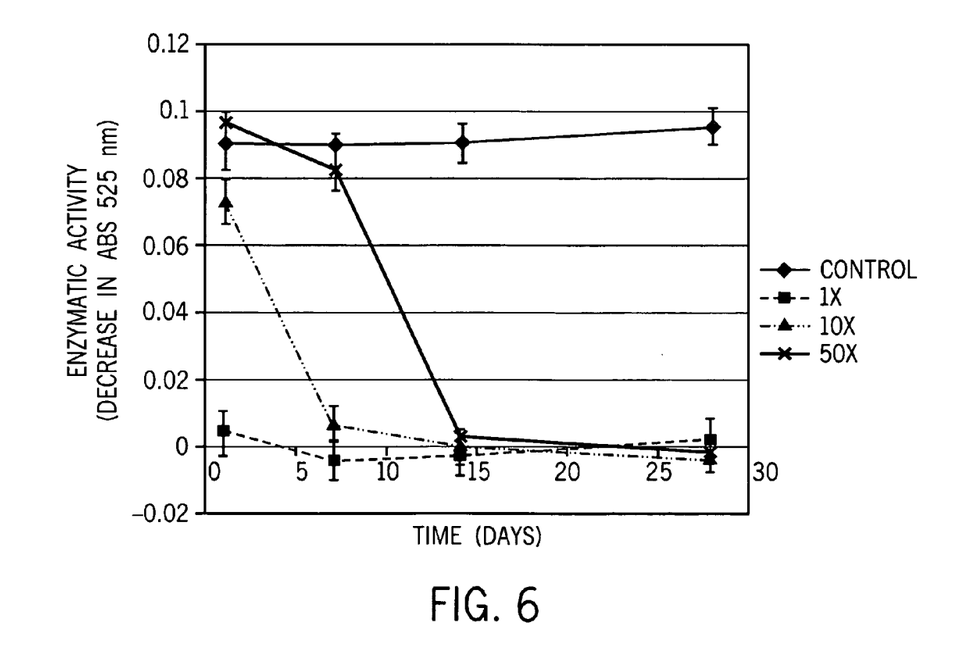
FIG. 6 shows the enzymatic activity of C-ABC after release from microparticles. Data points are differences between two means. Error bars represent pooled standard deviations.

The data in FIG. 6 represent decreases in absorbance at 525 nm., corresponding to a decrease in ChS-A concentration and an increase in C-ABC activity. Data are shown as the difference between experimental and negative control (blank microparticle) values. Control values were generated by taking the positive control and subtracting the negative control.

As shown in FIG. 6, C-ABC retained biological activity after release from microparticles. Activity increased with an increase in C-ABC loading, and activity persisted for longer periods of time as loading was increased. However, up until 30 days, no activity was seen beyond 7 days.

These results indicate that biologically active C-ABC can be released from polymer microparticles, but that higher loading or changes in fabrication techniques may be required for sustained release. Sustained delivery will be of particular importance for treatment of nervous system injuries, because injury mechanisms resulting in glial scarring may persist for long periods of time after the initial trauma.

Enzymatic activity may be lost due to high temperatures, pH changes, protease activity, or shearing during mixing. Activity measurements should be compared with concentrations of released enzyme; however, measurements of absolute concentration require tagging of the molecule.

Therefore, Chondroitinase ABC retains its activity after release from polymer microparticles, making polymeric delivery a feasible technique for clinical treatment of disc herniation and brain, spinal cord, and peripheral nerve injuries.

Example 3

3A. Introduction

Strategies were developed to promote axonal regeneration by manipulating the structural, cellular, and molecular environment of the spinal cord. Computer aided design has been used to facilitate fabrication of grafts from the biodegradable polymer polylactide-glycolic acid. In one form, grafts were 3 millimeters in diameter and 3 millimeters in length and contained seven parallel-aligned channels of 450 micrometers diameter. Primary Schwann cells ($120\times10^6$ cells/ml. in Matrigel) were microinjected into these channels. It has been demonstrated that cells survive in this environment for 48 hours in vitro. Schwann cell loaded channels were then inserted into a 3 millimeter gap between the transected ends of rat spinal cords at T8–10 level. Cords were harvested at 1, 2 and 3 months after implantation of the grafts and sectioned transverse or longitudinal to the spinal cord axis. Immunostaining against neurofilament light chain demonstrated axonal growth throughout the length of the channels (>2700 micrometers). In each channel, there were 89.9±15 (mean, standard deviation) axons.

In separate experiments, chondroitinase—ABC (C-ABC) was incorporated in PLGA microspheres using a water-oil-water, double emulsion solvent extraction technique. C-ABC has been demonstrated to promote regeneration in spinal cord. In vitro studies demonstrated that these microspheres degrade gradually and release the active enzyme for up to 7 days. Release kinetics of C-ABC can be manipulated by changing the molecular weight of PLGA, the ratio of lactide to glycolide in the copolymer, thickness and porosity of the PLGA coat.

Therefore, biocompatible, biodegradable polymer grafts support axonal growth in the spinal cord. The structural geometry of the conduits, cell content, and release of C-ABC, and other bioactive agents administered systemically or time-released into the microenvironment can be independently manipulated to define optimal conditions for promoting spinal cord functional regeneration.

3B. Experimental Procedure

The spinal cord of a Sprague-Dawley rat was exposed at T9. A 3 mm. segment of cord was removed and a PLGA implant was inserted between the cut ends. A split micropipette tip was sutured to the spinous processes above and below the T8–10 laminectomy to provide stability. This example was dissected 1 month after surgery and prepared in bleach for demonstration. After removal of the spine, pins were placed at the upper and lower levels of the laminectomy to confirm position by x-ray.

Light and electron micrographs were prepared. The Schwann cells isolated from 3-day rat sciatic nerves are gold/brown upon S-100 staining, and fibroblasts unstained. Light micrographs were taken of cresyl violet stained Schwann cells in channels of the implant at 400× and 630×. Sections were taken through one of the seven channels in a PLGA graft. Electron micrographs of the same area were taken and showed a viable cell with typical Schwann cell morphology; specifically, the chromatin is loosely packed with areas of condensation in the sub-membranous regions of the nucleus. The cell is rounded and surrounded by Matrigel.

Animals were examined weekly by blinded observers using a standardized locomotor scoring system (Beatty-Bresnahan-Basso: BBB scale). Each data point was the mean of scores by three independent, blinded observers. Six groups of animals were studied. Sham-operated animals have a normal BBB score of 21 which did not change during this 4-week observation period. Treated groups all had scaffolds implanted containing Matrigel, SpL 201 cells, or Schwann cells. Schwann cells were implanted into scaffolds with 450 micrometer or 660 micrometer channels. Animals with 660 micrometer channels achieved slightly more mobility.

Experiments were conducted comparing the ability of different cell types to support axonal growth through PLGA scaffolds. In each case, the micrograph or data order to the mid point of the scaffold between the rostral and caudal spinal cord stumps. Micrographs were taken of: (A) channels seeded with P5 rat Schwann cells stained with an antibody directed against neurofilament proteins; (B) an adjacent section stained with an antibody to S100, a Schwann cells marker demonstrating that the graft is populated with Schwann cells; (C) S100 stained channels from the graft seeded with Matrigel alone showing absence of staining; (D) a neurofilament stained section from a channel seeded with SpL 201 cells (an immortalized rat Schwann cells precursor line), and the density of neurofilament staining was less than in A; (E) neurofilament stained sections from channels seeded with Matrigel alone showing minimal staining; and (F) neurofilament stained sections from channels seeded with fibroblasts showing absence of staining. Table 1 shows the number of neurofilament stained axons at the mid-point of the scaffold counted by a blinded observer.

TABLE 1

|  | Matrigel alone | Fibroblasts | SpL 201 cells | Schwann cells |
|---|---|---|---|---|
| Total axons (mean; SEM) | 12 ± 7 | 0 ± 0 | 158 ± 46 | 449 ± 36 |
| No. of Animals/ Channels counted | 1/6 | 1/7 | 5/35 | 2/11 |

In another experiment, photographs were taken one month after cord transection and implantation of a PLGA graft containing Matrigel and Schwann cells. The channels were filled with axons (brown neurofilament immunostaining on the photographs) and capillary loops. Axons were shown entering a channel from the cord stump.

It can be seen that the inventors have systematically: (i) optimized the structure of the microenvironment by constructing biodegradable poly DL-lactic-co-glycolic acid polymer implants with multiple parallel channels; (ii) optimized the cellular environment by using Schwann cells within the channels; (iii) optimized the molecular environment by using the biodegradable implant as a sustained release source of chondroitinase ABC; and (iv) used this system to test the ability of different cell types to support axonal regeneration.

Thus, it has been demonstrated that biodegradable polymer implants with defined micro-architecture can be designed and fabricated for use as a scaffold. Supporting cells known to promote central nervous system axonal growth can be seeded into and survive in the channels of these scaffolds. The polymer implants are compatible with spinal cord tissue, and the polymer material can be used as a reservoir for the slow, sustained release of bioactive molecules such as chondroitinase ABC. It has been shown that axons will grow through the channels of the polymer scaffold. Animals with the polymer grafts did not experience any more adverse events (such as infections) than controls. In experiments, wild-type Schwann cells supported axonal growth better than immortalized Schwann cells precursors (SpL 201), fibroblasts or Matrigel alone. The invention allows for systematic and independent manipulation of the structural, cellular, and molecular components of the environment in the regenerating spinal cord. By using different individual, or mixes of supporting cells, growth promoting agents, and blockers of growth inhibition, it is possible to provide a regeneration-supportive environment.

Therefore, it can be seen that the invention provides a biodegradable polymer device for surgical implantation with therapeutic value for the treatment of spinal cord injury. The biodegradable polymer implant functions both as a scaffold to support axon growth across a gap and as a site for the controlled local delivery of agents that promote axon regeneration and successful target acquisition.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. An implant for bridging a gap in a severed spinal cord or nerve and for promoting nerve regeneration, the implant comprising:
    a matrix comprising a biocompatible, biodegradable, polymeric material and a bioactive agent dispersed within the matrix, the matrix having a proximal end for connection to a first end of a severed spinal cord or nerve and a distal end for connection to a second end of the severed spinal cord or nerve,
    wherein the matrix includes a plurality of internal guidance channels extending between the proximal end of the matrix and the distal end of the matrix to facilitate rejoining of the first end of the severed spinal cord or nerve and the second end of the severed spinal cord or nerve, and
    wherein the bioactive agent is a proteoglycan degrading enzyme, and
    the guidance channels are spaced apart adjacent a perimeter of the matrix at the proximal end of the matrix and converge inward toward the axis of the matrix at the distal end of the matrix.

2. The implant of claim 1 wherein:
the polymeric material is poly(lactide-co-glycolide).

3. The implant of claim 1 further comprising:
Schwann cells disposed within at least one of the plurality of guidance channels.

4. The implant of claim 1 wherein:
the proteoglycan degrading enzyme is chondroitinase.

5. The implant of claim 4 wherein:
the chondroitinase is chondroitinase ABC.

6. The implant of claim 1 wherein:
biocompatible, biodegradable, polymeric microspheres including a second bioactive agent are disposed within at least one of the plurality of guidance channels.

7. The implant of claim 6 wherein:
the microspheres comprise poly(lactide-co-glycolide).

8. The implant of claim 6 wherein:
the second bioactive agent is a proteoglycan degrading enzyme.

9. The implant of claim 8 wherein:
the proteoglycan degrading enzyme is chondroitinase.

10. The implant of claim 9 wherein:
the chondroitinase is chondroitinase ABC.

11. The implant of claim 1 wherein:
the guidance channels are arranged such that the guidance channels correspond to spinal cord tracts when the implant is positioned in a gap in a severed spinal card.

12. The implant of claim 1 wherein:
Schwann cells disposed within at least one of the plurality of guidance channels, and
biocompatible, biodegradable, polymeric microspheres including a second bioactive agent other than Schwann cells are disposed within at least one of the plurality of guidance channels.

13. The implant of claim 1 wherein:
Schwann cells disposed within at least one of the plurality of guidance channels, and
a second bioactive agent other than Schwann cells is disposed within at least one of the plurality of guidance channels.

14. An implant for bridging a gap in a severed spinal cord or nerve and for promoting nerve regeneration, the implant comprising:
    a matrix comprising a biocompatible, biodegradable, polymeric material, the matrix having a proximal end for connection to a first end of a severed spinal cord or nerve and a distal end for connection to a second end of the severed spinal cord or nerve,
    wherein the matrix includes a plurality of internal guidance channels extending between the proximal end of the matrix and the distal end of the matrix to facilitate rejoining of the first end of the severed spinal cord or nerve and the second end of the severed spinal cord or nerve, and
    wherein a bioactive agent other than Schwann cells is disposed in at least one of the guidance channels, and
    wherein the bioactive agent is a proteoglycan degrading enzyme, and
    the guidance channels are spaced apart adjacent a perimeter of the matrix at the proximal end of the matrix and converge inward toward the axis of the matrix at the distal end of the matrix.

15. The implant of claim 14 wherein:
the proteoglycan degrading enzyme is chondroitinase.

16. The implant of claim 15 wherein:
the chondroitinase is chondroitinase ABC.

17. The implant of claim 14 wherein:
the bioactive agent in included within biocompatible, biodegradable, polymeric microspheres disposed within at least one of the plurality of guidance channels.

18. The implant of claim 17 wherein:
the microspheres comprise poly(lactide-co--glycolide).

19. The implant of claim 17 wherein:
the microspheres are suspended in a carrier.

20. The implant of claim 17 wherein:
the proteoglycan degrading enzyme is chondroitinase.

21. The implant of claim 20 wherein:
the chondroitinase is chondroitinase ABC.

22. The implant of claim 14 wherein:
the guidance channels are arranged such that the guidance channels correspond to spinal cord tracts when the implant is positioned in a gap in a severed spinal cord.

23. An implant for bridging a gap in a severed spinal cord or nerve and for promoting nerve regeneration, the implant comprising:
a matrix comprising a biocompatible, biodegradable, polymeric material, the matrix having a proximal end for connection to a first end of a severed spinal cord or nerve and a distal end for connection to a second end of the severed spinal cord or nerve,
wherein the matrix includes a plurality of internal guidance channels extending between the proximal end of the matrix and the distal end of the matrix to facilitate rejoining of the first end of the severed spinal cord or nerve and the second end of the severed spinal cord or nerve, and
wherein the guidance channels are spaced apart adjacent a perimeter of the matrix at the proximal end of the matrix and converge inward toward the axis of the matrix at the distal end of the matrix.

24. The implant of claim 23 wherein:
Schwann cells disposed within at least one of the plurality of guidance channels, and
biocompatible, biodegradable, polymeric microspheres including a bioactive agent other than Schwann cells are disposed within at least one of the plurality of guidance channels.

25. The implant of claim 24 wherein:
the bioactive agent is a proteoglycan degrading enzyme.

26. The implant of claim 23 wherein:
Schwann cells disposed within at least one of the plurality of guidance channels, and
a bioactive agent other than Schwann cells is disposed within at least one of the plurality of guidance channels.

27. The implant of claim 26 wherein:
the bioaotive agent is a proteoglycan degrading enzyme.

* * * * *

UNITED STATES PATENT AND TRADEMARK OFFICE
CERTIFICATE OF CORRECTION

| | |
|---|---|
| PATENT NO. | : 7,163,545 B2 |
| APPLICATION NO. | : 10/629427 |
| DATED | : January 16, 2007 |
| INVENTOR(S) | : Michael J. Yaszemski et al. |

It is certified that error appears in the above-identified patent and that said Letters Patent is hereby corrected as shown below:

Col. 12, line 17
In claim 11, "card" should read -- cord --.

Col. 14, line 19
In claim 27, "bioaotive" should read -- bioactive --.

Signed and Sealed this

Thirty-first Day of July, 2007

JON W. DUDAS
*Director of the United States Patent and Trademark Office*